US009902659B2

(12) United States Patent
Rothaemel et al.

(10) Patent No.: US 9,902,659 B2
(45) Date of Patent: Feb. 27, 2018

(54) PROCESS AND PLANT FOR PRODUCING OLEFINS FROM OXYGENATES

(71) Applicant: L'Air Liquide, Societe Anonyme pour l'Etude et l'Exploitation des Procedes Georges Claude, Paris (FR)

(72) Inventors: Martin Rothaemel, Frankfurt am Main (DE); Roberta Olindo, Frankfurt am Main (DE); Stephane Haag, Frankfurt (DE); Thomas Renner, Frankfurt am Main (DE); Frank Castillo-Welter, Friedrichsdorf (DE)

(73) Assignee: L'AIR LIQUIDE SOCIETE ANONYME POUR L'ETUDE ET L'EXPLOITATION DES PROCEDES GEORGES CLAUDE, Paris (FR)

( * ) Notice: Subject to any disclaimer, the term of this patent is extended or adjusted under 35 U.S.C. 154(b) by 154 days.

(21) Appl. No.: 14/768,575

(22) PCT Filed: Feb. 4, 2014

(86) PCT No.: PCT/EP2014/052163
§ 371 (c)(1),
(2) Date: Aug. 18, 2015

(87) PCT Pub. No.: WO2014/124844
PCT Pub. Date: Aug. 21, 2014

(65) Prior Publication Data
US 2016/0145169 A1 May 26, 2016

(30) Foreign Application Priority Data
Feb. 18, 2013 (DE) .................. 10 2013 101 577

(51) Int. Cl.
C07C 1/20 (2006.01)
C07C 5/11 (2006.01)
(Continued)

(52) U.S. Cl.
CPC ............... C07C 1/20 (2013.01); B01J 19/245 (2013.01); C07C 5/11 (2013.01); C10G 3/42 (2013.01);
(Continued)

(58) Field of Classification Search
CPC ......... C07C 1/20; C07C 5/11; C07C 2529/40; B01J 19/245; B01J 2219/24; C10G 3/42; C10G 45/44
See application file for complete search history.

(56) References Cited

U.S. PATENT DOCUMENTS 4,482,772 A 11/1984 Tabak
4,543,435 A 9/1985 Gould et al.
(Continued)

FOREIGN PATENT DOCUMENTS

DE 102005048931 4/2007
WO WO 2006 136433 12/2006
WO WO 2011 131647 10/2011

OTHER PUBLICATIONS

International Search Report for PCT/EP2014/052163 dated Apr. 9, 2014.

Primary Examiner — Brian McCaig
Assistant Examiner — Jason Chong
(74) Attorney, Agent, or Firm — Justin K. Murray

(57) ABSTRACT

A process for producing olefins from oxygenates includes the following steps:
(i) heterogeneously catalyzed conversion of at least one oxygenate to a stream containing propylene, aromatics and cyclic olefins, (Continued)

(ii) at least partial hydrogenation of the aromatics and cyclic olefins to naphthenes, and
(iii) at least partial recirculation of the naphthenes into the heterogeneously catalyzed conversion.

11 Claims, 2 Drawing Sheets

(51) Int. Cl.
    *C10G 45/44*     (2006.01)
    *C10G 3/00*     (2006.01)
    *B01J 19/24*     (2006.01)

(52) U.S. Cl.
    CPC ........... *C10G 45/44* (2013.01); *B01J 2219/24* (2013.01); *C07C 2529/40* (2013.01)

(56) References Cited

U.S. PATENT DOCUMENTS

| | | | |
|---|---|---|---|
| 5,773,670 A * | 6/1998 | Gildert | B01D 3/009 203/DIG. 6 |
| 2004/0039239 A1 | 2/2004 | Shutt | |
| 2006/0063956 A1 | 3/2006 | Kalnes et al. | |
| 2006/0161035 A1 | 7/2006 | Kalnes et al. | |
| 2007/0284284 A1 | 12/2007 | Zones et al. | |
| 2011/0319686 A1* | 12/2011 | Rothaemel | C07C 1/20 585/312 |
| 2012/0102829 A1* | 5/2012 | Rothaemel | C10G 29/22 44/447 |

* cited by examiner

PROCESS AND PLANT FOR PRODUCING OLEFINS FROM OXYGENATES

CROSS REFERENCE TO RELATED APPLICATIONS

This application is a § 371 of International PCT Application PCT/EP2014/052163, filed Feb. 4, 2014, which claims the benefit of DE 10 2013 101 577.8, filed Feb. 18, 2013, both of which are herein incorporated by reference in their entireties.

TECHNICAL FIELD OF THE INVENTION

The present invention relates to a process for producing olefins from oxygenates, with the following steps: (i) heterogeneously catalyzed conversion of at least one oxygenate to a stream containing propylene, aromatics and cyclic olefins, and (ii) at least partial hydrogenation of the aromatics and cyclic olefins to naphthenes. Furthermore, the invention comprises a plant for carrying out this process.

BACKGROUND

Propene ($C_3H_6$), often also referred to as propylene, is one of the most important starting substances of the chemical industry. The demand for the base material propylene is increasing worldwide, wherein propylene just like ethylene mostly is produced from petroleum in a steam cracker in a ratio dependent on the process conditions and the raw materials.

To obtain additional propylene, a number of processes exist, such as the PDH process which proceeds from propane as educt. What is known, however, above all is the so-called MTP process, in which olefins are produced from methanol (MeOH) or dimethyl ether (DME) by catalytic conversion on a zeolitic catalyst. By varying the catalyst and the process conditions, the selectivity of the products obtained can be influenced and the product spectrum thus can be shifted towards short-chain olefins (then often also the process name Methanol-to-Olefin (MTO)), towards longer-chain products (then often also the process name Methanol-to-Gasoline (MTG)) or towards propylene.

The fundamentals of an MTP process are described for example in DE 10 2005 048 931 A1. From an educt mixture containing steam and oxygenates, such as methanol and/or dimethyl ether, $C_2$ to $C_4$ olefins are produced above all. By a heterogeneously catalyzed reaction in at least one reactor, the educt mixture is converted to a reaction mixture comprising low-molecular olefins and gasoline hydrocarbons. By a suitable separation concept, higher olefins, above all the $C_{5+}$ fraction, can at least partly be recirculated into the reactor as recycling stream and in said reactor for the most part be converted to propylene, whereby the propylene yield is increased.

The MTP process usually has a propylene yield of about 65% (mole C). An increased yield would distinctly improve the economy of the process. As predominant by-product in the MTP process a gasoline-like mixture (MTP gasoline) is obtained, which substantially consists of olefins, paraffins, cycloparaffins, cycloolefins and aromatics. This MTP gasoline likewise can be incorporated into a succeeding value chain, but has a lower market price than propylene.

As described in WO 2006/136433 A1 it therefore partly is attempted to subject the MTP gasoline to a post-processing in the form of an olefin interconversion, in which the MTP gasoline is converted on a zeolitic catalyst at temperatures of about 400 to 500° C. and a pressure of 1 to 5 bar. Due to this downstream reaction, a moderate increase of the propylene yield of the entire process can be achieved, but the total yield still lies below 70 mol-%.

A direct recirculation of the MTP gasoline into the MTP reactor provides no increase in the yield of propylene. Since undesired alkylation reactions of the aromatics occur inside the MTP reactor, by which methanol is consumed, which then no longer would be available for the selective formation of propylene, the propylene yield of the entire process even would decrease.

Some processes therefore aim at converting the heavier olefins obtained, so that at least a product with homogeneous composition and higher market price is obtained. U.S. Pat. No. 4,543,435 for example teaches that at least a part of the olefins obtained is to be converted to heavy hydrocarbons, so that the yield of liquefied gas and gasoline can be increased within the MTP process.

WO 2011/131647 describes a process for producing aromatic hydrocarbons, in which a feed of light alkanes is at least partly converted to aromatics on a suitable catalyst. Parallel thereto an MTO process takes place. A part of the oxygenate feed of the MTO process is produced in that the hydrogen obtained during the conversion of the alkanes to aromatics is converted to an oxygenate with carbon monoxide and/or carbon dioxide. The product streams thus obtained can easily be combined with the other by-products of the MTP process, above all methane, carbon oxides, hydrogen and a product similar to liquefied gas.

For increasing the yield of valuable products from an MTP process, a hydrogenation of the aromatic hydrocarbons obtained also is known. US 2004/0039239 for example teaches that higher olefins are to be hydrogenated on a suitable hydrogenation catalyst. In particular due to the fact that aromatics also are hydrogenated to paraffins, the yield of a gasoline-like valuable product thus can be increased.

From U.S. Pat. No. 4,482,772 a hydrogenation within an MTP process is known, in which first the conversion of the oxygenates to olefins takes place and the olefins thus obtained subsequently are oligomerized. Subsequent to the oligomerization, at least parts of the product stream are hydrogenated, whereby aromatics contained in the product stream are converted to naphthenes. The yield of a gasoline-like valuable product likewise can be increased thereby.

For carrying out such hydrogenations, various types of catalyst and their possible applications are known for example from US 2007/0284284 A1.

However, since all by-products of the MTP process thus obtained have a lower market value than the actual target product propylene, it can only partly be compensated with this process that the propylene yield maximally is about 65%.

SUMMARY OF THE INVENTION

Therefore, it is the object of the present invention to provide a process in which proceeding from oxygenates the propylene yield can distinctly be increased.

This object is solved by a process with the features of the claims.

In a first step of an embodiment of the invention, the oxygenates therefore are heterogeneously catalytically converted to a stream containing propylene, aromatics and cyclic olefins (in the following referred to as oxygenate conversion reaction). Preferably, the oxygenates contain methanol; in a particularly preferred embodiment of the invention the oxygenate stream consists of methanol for more than 99 vol-%. However, the use of crude methanol (max. 30% water), pure DME or DME/methanol mixtures also is possible. In a second step, the aromatics and cyclic olefins obtained are hydrogenated to naphthenes (also called cycloparaffins) (in the following referred to as hydrogenation reaction). In a third step, the cycloparaffins thus obtained then are at least partly recirculated into the heterogeneously catalyzed conversion of the oxygenates. The hydrogenation is necessary as otherwise the aromatics would be alkylated by methanol during the recirculation (see above), whereas the cyclic olefins can disproportionate in the reactor, where by 2 mol of cycloolefin each there would each be formed 1 mol of aromatic and 1 mol of paraffin (but no propylene or other olefins). The cyclic paraffins obtained in the second step according to the invention then can be recirculated into the heterogeneously catalyzed conversion, where they are converted in a known way to olefins with a shorter chain length, in particular to propylene, by an olefin interconversion, without undesired alkylation reactions occurring, since the cycloparaffins already exactly correspond to olefins in terms of their empirical chemical formula ($C_nH_{2n}$). After ring opening, the conversion is effected with moderate turnover, but good selectivity to $C_2$ to $C_4$ olefins.

For the hydrogenation reaction, hydrogen ($H_2$) advantageously is used as hydrogenating agent. Since the aromatics and cyclic olefins originate from the MTP reaction, they include no inorganic catalyst poisons such as sulfur etc. Thus, very moderate conditions at temperatures of less than 150° C. and pressures of less than 25 bar can be used for the hydrogenation, in order to achieve an almost complete conversion. There can be used standard hydrogenation catalysts, which contain e.g. nickel or palladium as active component which is applied on a carrier, e.g. activated carbon.

Moreover, it was found to be advantageous to carry out the hydrogenation such that the ratio between hydrogenated product and non-hydrogenated feed stream, which contains aromatics and cyclic olefins, lies between 1:1 and 10:1 (by weight). By setting this ratio, a dilution of the educts to be converted can be achieved. This is necessary because the hydrogenation is a strongly exothermal reaction and otherwise too strong heating of the reaction mixture occurs within the hydrogenation. The use of hydrogenated product as diluent has the advantage that in this way no further components are introduced into the process. In the hydrogenated product a distinction must be made between liquid product streams and gaseous product streams, which substantially consist of non-converted hydrogen and formed light gases. Due to the greater density it is advantageous to use the liquid product for diluting the hydrogenation.

The molar excess of hydrogen should lie between 200 and 5000% of the quantity theoretically necessary for the complete saturation of all existing double and aromatic bonds. Thus, a limitation of the reaction due to local hydrogen concentrations can completely be excluded.

By separating hydrogen after the hydrogenation, the excess of hydrogen is irrelevant for the further processing of the hydrogenated stream, and the non-converted hydrogen also can be recirculated into the hydrogenation, so that actually no increased hydrogen consumption occurs. Correspondingly, only the stoichiometrically necessary quantity of hydrogen must be added continuously. An enrichment of gaseous by-products of the hydrogenation, such as e.g. methane, can be controlled in that a continuous small purge stream is removed from the process part.

Furthermore, it was found to be advantageous to separate a $C_5$ fraction from the remaining residual stream already after the heterogeneously catalyzed conversion (step (i)). Thus, the particularly valuable low-molecular olefins, in particular the propylene itself, can immediately be withdrawn from the product stream of the heterogeneously catalyzed conversion, which is why all succeeding plant components for the processing of the higher olefins can be dimensioned smaller.

The separation advantageously is effected by cooling, in which the $C_5$ fraction remains gaseous and due to its state of matter separates from the remaining liquid residual stream. The energy thus gained can be utilized at some other point in the process.

From the remaining residual stream an aqueous fraction containing oxygenates is obtained on the one hand, and on the other hand a $C_{5+}$ fraction. Preferably, this is achieved by a simple phase separation, whereby high energy costs, as they are incurred for example by a distillation, can be saved. At least parts of this $C_{5+}$ fraction then are supplied to the hydrogenation (step (ii)). As a result, the stream of the longer-chain olefins virtually contains no water and molecules with highly reactive OH groups which might lead to undesired side reactions during the hydrogenation.

Advantageously, the aqueous fraction containing oxygenates is subjected to a separation process, in which the oxygenates and the water are separated from each other. This separation preferably is effected in a distillation, in order to ensure a sufficient separation sharpness. At least parts of the water are discharged from the process. Separated methanol and/or separated water can be recirculated into the heterogeneously catalyzed conversion (step (i)). The recirculation of the water preferably is effected as steam.

In a particularly preferred configuration of the entire process the oxygenate conversion is effected in two stages, wherein in the first stage the at least one oxygenate first is/are converted to at least one corresponding ether and in the second stage the ether(s) is/are converted to olefins. When methanol is used as oxygenate, a conversion of the methanol to dimethyl ether first is effected and subsequently the conversion of the dimethyl ether to propylene and other olefins, in particular also to aromatics and cyclic olefins. In this two-stage configuration it is recommendable to recirculate the oxygenate, preferably the methanol, already to before the first stage, i.e. before the conversion to dimethyl ether, while the vaporous water is introduced between the first and the second stage, as it must first be used as educt for the conversion of the ether to olefins. Thus, in the first stage no unnecessary water is used, which negatively influences the equilibrium reaction during the etherification; the steam however is available as educt in the olefin formation.

The product from the oxygenate conversion reaction initially is cooled by means of methods known to the skilled person, wherein water and water-soluble components such as oxygenates (methanol, DME) are condensed out and thus can easily be separated from the remaining hydrocarbon product. The resulting aqueous stream then is supplied to a suitable separating means (e.g. a distillation column), wherein the oxygenates are recirculated into the first reaction stage, as described above. The amount of water resulting from the conversion of the oxygenates is removed from the process, while the residual amount is recirculated to before the second reaction stage, as described above, so that closed circuits are obtained for the most part.

The largely water-free hydrocarbon stream is compressed after the cooling; there is obtained a pressurized light hydrocarbon stream and a liquid, likewise pressurized heavy hydrocarbon stream. To safely separate possibly still contained lighter olefins, it is recommendable to switch a further separation stage in which possibly still contained $C_{4-}$ fractions can be removed from the $C_{5+}$ fraction. Advantageously, this separation stage is a distillation, in order to ensure a sufficient separation sharpness. In accordance with a development of the invention it is also recommendable to separate the $C_{7-}$ fraction from the $C_{7+}$ fraction after the heterogeneously catalyzed conversion (step (i)). At least parts of the $C_{7+}$ fraction then are supplied to the hydrogenation (step (ii)). It can thereby be ensured that exclusively that stream which contains the aromatics and cyclic olefins to be hydrogenated is supplied to the hydrogenation and the same thus can be dimensioned correspondingly small.

According to the invention, at least parts of the $C_{7-}$ fraction are recirculated into the heterogeneously catalyzed conversion (step (i)), since the $C_{7-}$ fraction contains no or hardly any systems which cannot be converted to short-chain olefins within the heterogeneously catalyzed conversion. The yield of propylene can further be increased thereby.

In particular, it was found to be advantageous to feed parts of the $C_{7-}$ fraction just like the hydrogenated naphthenes from step (ii) in the case of a two-stage heterogeneously catalyzed conversion between the conversion of the oxygenates into ethers and the conversion of the ethers into the olefins. Due to the fact that the longer-chain olefins thus are fed in only after the etherification, the conversion of the oxygenates to the associated ether can be designed smaller, and in the conversion of the oxygenates to the olefins the longer-chain olefins nevertheless are subjected to a conversion towards short-chain products.

Furthermore, it was found to be advantageous when the separation of the $C_{7-}$ from the $C_{7+}$ fraction is effected from the previously separated $C_{5+}$ fraction. This has the advantage that due to the early separation of the $C_{5-}$ fraction, the guided streams are distinctly smaller and the apparatus expenditure thus becomes smaller.

Embodiments of the present invention may furthermore comprise a plant with the features of claim 26. Such plant is particularly useful for carrying out a process according to any of the method claims. Such plant comprises a reactor for the heterogeneously catalyzed conversion of an oxygenate to a stream containing propylene, aromatics and cyclic olefins, a reactor for the hydrogenation of the aromatics and cyclic olefins to naphthenes, and a conduit for the at least partial recirculation of the naphthenes into the reactor for the heterogeneously catalyzed conversion. With this plant it can be achieved that aromatics and double-bond systems are hydrogenated and the cyclic paraffins thus obtained can be recirculated into the catalytic conversion, where the catalyst used there brings about an olefin interconversion, so that short-chain olefins are obtained, in particular also the valuable product propylene. A further advantage of this plant design consists in that already existing plants can be retrofitted with a reactor for the hydrogenation of the aromatics and cyclic olefins as well as the return conduit, so that the propylene yield also can be increased with existing plants.

Further developments, advantages and possible applications of the invention can also be taken from the following description of the Figures and the Example. All features described and/or illustrated form the subject-matter of the invention per se or in any combination, independent of their inclusion in the claims or their back-reference.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION

Figure 1:
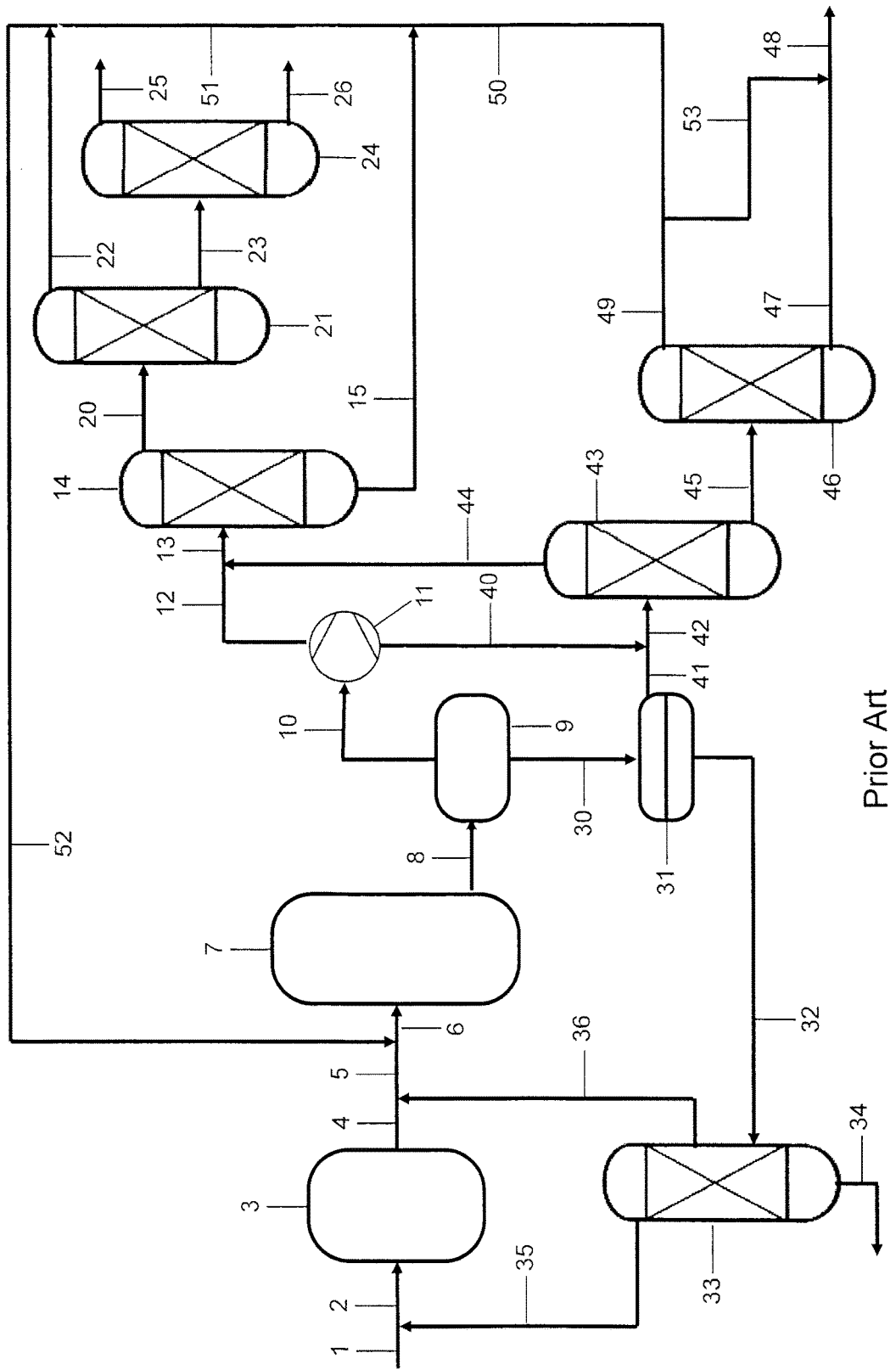
FIG. 1 shows the schematic representation of a usual MTP process.

FIG. 1 shows the MTP production according to the prior art. Via conduits 1 and 2, methanol is introduced into a reactor 3 in which the methanol is at least partly converted to dimethyl ether. Via conduits 4, 5 and 6, the dimethyl ether is withdrawn and supplied to a second reactor 7 in which the dimethyl ether together with steam is converted to olefins. The olefin stream thus obtained contains propylene and other olefins, but also cyclic olefins and aromatics.

Via conduit 8, the product stream obtained is introduced into the cooling device 9. There, a gaseous phase separates from a liquid phase. The gaseous phase contains the $C_{5-}$ fraction and is supplied to a compressor 11 via conduit 10. The gaseous fraction obtained in the compressor 11 is supplied to a distillation column 14 via the conduits 12 and 13. In this distillation column 14, the $C_{3-}$ fraction is separated from the $C_{4+}$ fraction.

Via conduit 20, the $C_{3-}$ fraction is supplied to a column 21 in which the $C_{2-}$ fraction is withdrawn over the head. Via conduit 22 and conduit 52, the $C_{2-}$ fraction gets back into conduit 5 and from there can be guided via conduit 6 into the reactor 7, so that here the desired product propylene is at least partly produced by olefin interconversion. To avoid an enrichment of inert light gaseous components such as methane or $CO_x$ in the circuit, a small partial quantity of the stream from conduit 22 can be removed from the system as purge via a non-illustrated conduit. Furthermore, the $C_3$ fraction is withdrawn from the column 21 via conduit 23 and supplied to a column 24. In this column 24, the desired target product propylene is distilled off over the head and withdrawn via conduit 25, while in the bottom further compounds with three carbon atoms are left and are withdrawn via conduit 26.

Via conduit 15, the bottom product of the column 14 is withdrawn from the column 14 as $C_4$ fraction, and via the conduits 51 and 52 it is likewise recirculated to before the conversion of the ether to olefins in conduit 5, in order to further increase the yield of propylene by olefin interconversion. To avoid an enrichment of butane (a component inert for the conversion in the reactor) in the circuit, a small partial quantity of the stream from conduit 15 can be removed from the system as purge via a non-illustrated conduit.

The liquid fraction obtained in the cooler 9 is supplied to a separator 31 via conduit 30. The aqueous phase separated in the separator 31 also contains oxygenates (when using methanol as educt, above all methanol) and is supplied to a column 33 via conduit 32.

From the bottom of the column 33 water is discharged via conduit 34. Furthermore, steam is withdrawn from the column 33 via conduit 36 and fed into conduit 4, from where the steam gets into the reactor 7 via conduit 5 and conduit 6, in which reactor it is used as educt for the conversion of the dimethyl ether to olefins.

The top product of the column 33, at least one oxygenate, preferably methanol, is fed into the conduit 1 via conduit 35 and thus gets into the reactor 3 via conduit 2. When methanol is used as educt, recovered methanol together with the methanol fed in as educt thus is converted to dimethyl ether. Alternatively, the oxygenate also can directly be returned into the reactor 7 together with the steam via conduit 36.

The organic phase withdrawn from the separator contains the $C_{5+}$ fraction, which is discharged via conduit 41 and passed on via a pump (not shown). To this $C_{5+}$ fraction, the liquid fraction obtained from the compressor 11 at 15-25 bar then is also admixed via conduit 40. The combined streams then are introduced into a column 43 via conduit 42. From the head of the column 43, the $C_{4-}$ fraction is introduced via conduit 44 into the conduit 12, from where it is fed into the column 14 together with the gaseous part from the compressor 11 via conduit 13.

Via conduit 45, the bottom product of the column 43, which contains the $C_{5+}$ fraction, is guided into the column 46. From the bottom of the column 46, the $C_{7+}$ fraction is withdrawn into the conduits 47 and 48.

Over the head of the column 46, the $C_5/C_6$ fraction obtained is recycled via the conduits 49, 50, 51 and 52, in that it is recirculated into the conduit 5. Parts of the $C_5$ and $C_6$ fraction are supplied to the conduit 47 via conduit 53 and discharged from the process via conduit 48 (purge). The stream leaving the process via conduit 48 represents the MTP gasoline.

Figure 2:
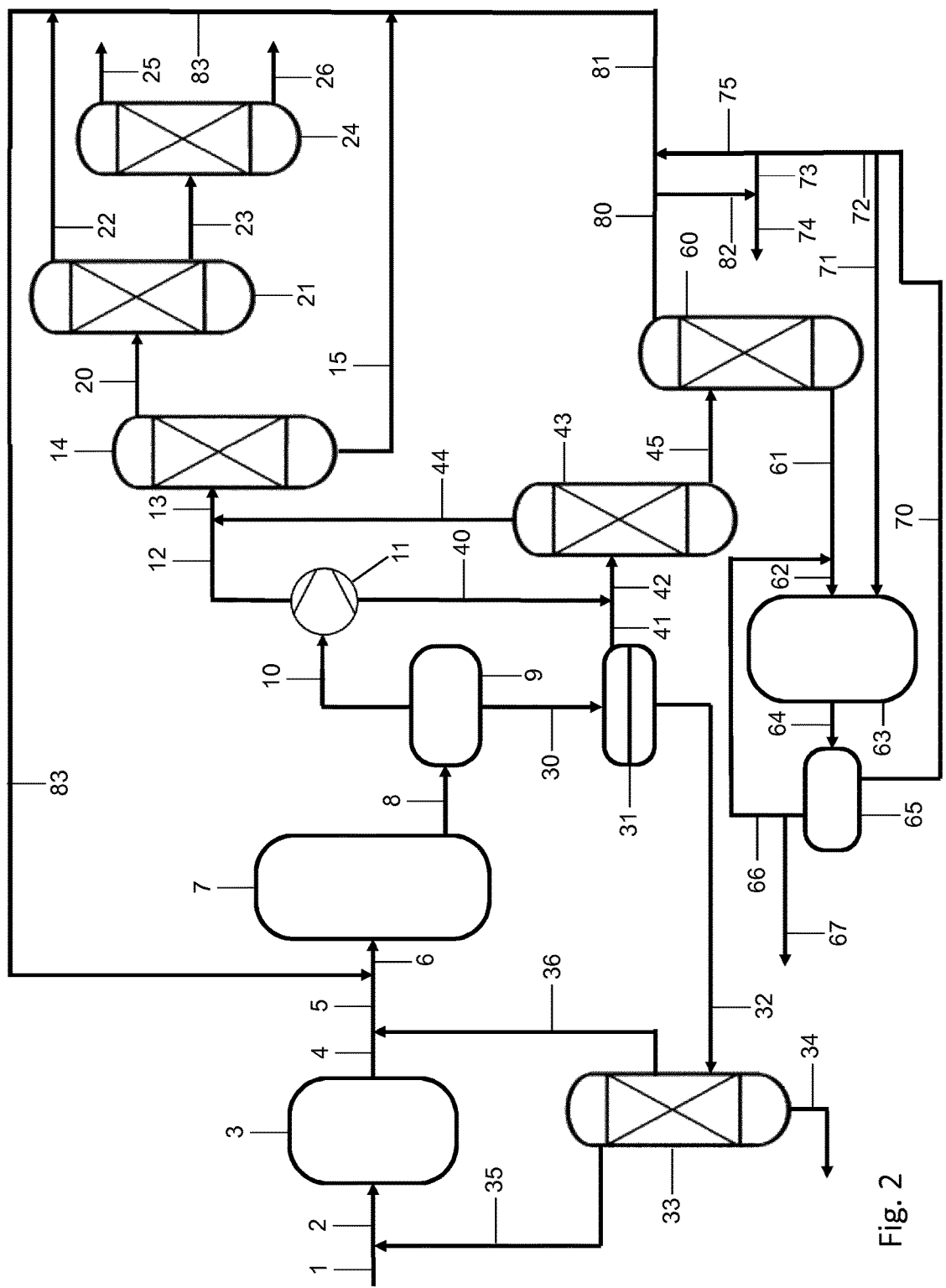
FIG. 2 shows the schematic representation of the process according to an embodiment of the invention.

FIG. 2 schematically shows the procedure of the process according to the invention. Up to the plant component 45, the process according to the invention corresponds to the process already known from the prior art.

Via conduit 45, the stream however is introduced into a column 60 in which the $C_{7-}$ fraction instead of the $C_5/C_6$ fraction is withdrawn over the head. In an advantageous configuration of the column 60, this column 60 is operated as extractive distillation and supplied with an additional stream which has advantageous chemical and physical properties, so that an even better separation between olefins in the head and aromatics and cyclic olefins in the bottom is possible. The stream used as extracting agent for example can be an olefin or a stream rich in aromatics, which preferably is produced and recirculated within the plant. The operating principle is based on the fact that either the olefins in the head or the aromatics in the bottom are enriched.

Via the conduits 80, 81 and 83, the $C_{7-}$ fraction is recirculated into the conduit 5 and thus before the reactor 7 for the conversion of the dimethyl ether to olefins, so that this stream can be subjected to an olefin interconversion. A small partial quantity of the stream 80 is removed from the system as purge via conduit 82, in order to limit the enrichment of inert components such as hexanes and heptanes in the circuit.

Due to the recirculation of the $C_{7-}$ stream, the propylene-yield olefin interconversion on the one hand is increased analogous to the following model reaction equation:

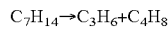

$$C_7H_{14} \rightarrow C_3H_6 + C_4H_8$$

The propylene yield also is increased indirectly, since the conversion of the $C_{7-}$ olefins proceeds endothermally, which in an advantageously adiabatically operated reactor reduces the increase in temperature, so that the selectivity of the total conversion to propylene is increased.

Via conduit 61, the $C_{7+}$ fraction is separated from the column 60, which then is supplied to the hydrogenation reactor 63 via conduit 62. The liquid hydrocarbon stream is heated to 20 to 250° C. and via a pressure of 2 to 45 bar mixed with hydrogen. The stream resulting therefrom then is introduced into a reactor 63 filled with a suitable hydrogenation catalyst.

The reactor 63 for example can be a constructively simple fixed-bed reactor, but there can also be used reactors with internal cooling, of the single- or multistage type. Noble metals just like nickel, palladium, platinum or mixtures thereof on carrier materials such as activated carbon, silica or alumina can be used as catalysts.

To ensure an advantageous configuration of the process in energetic terms, the hydrogenation reactor 63 is operated at approximately the same temperature as the bottom of the column 60, whereby an otherwise necessary heat exchanger between these two plant sections can be omitted, whereby the investment and operating costs of the process are reduced and the economy is improved.

After passage through the reactor 63, the cyclic olefins and the aromatics have been hydrogenated to naphthenes. Existing open-chain paraffins largely show an inert behavior in the hydrogenation. Possibly left small residual amounts of open-chain olefins are hydrogenated to the corresponding open-chain paraffins.

Via conduit 64, the product obtained is supplied to a cooling 65. In this cooling 65, the liquid phase at the same time is separated from the gas phase. The liquid phase is withdrawn from the cooling 65 via conduit 70. Since the hydrogenation is very exothermal, a part of the liquid phase is guided back into the hydrogenation reactor 63 via conduit 71. A dilution of the reaction mixture and thus an uncontrolled heating thereby can be avoided.

Via conduits 73 and 74, parts of this stream are discharged together with the partial stream 82 of the $C_{7-}$ product, in order to control the enrichment of inert components in the circuit. Due to its chemical composition of largely paraffinic components, the stream 74 also can be referred to as naphtha. The remaining stream of the cycloparaffins is recirculated into conduit 5 via conduits 75, 81, 82 and 83.

The gaseous part from the cooling stage 65 is fed back into conduit 61 via conduit 66, from where it gets into the hydrogenation reactor 63 via conduit 62. Since this hydrogen stream also contains formed light gases such as methane, a partial stream also must again be removed from the circuit at this point via conduit 67 (purge).

Due to the two recirculations via conduit 71 and conduit 66, a typical quantity ratio of 1 to 10 tons of hydrogenated liquid product per ton of non-hydrogenated feed is obtained in the hydrogenation reactor 63, and a molar excess of hydrogen in the amount of 2 to 50 times the theoretical hydrogen quantity required for the complete saturation of all double and aromatic bonds.

The liquid product which is withdrawn via conduit 70 substantially consists of open-chain and cyclic paraffins, which upon recirculation into the reactor 7 are converted to propylene and other short-chain olefins. The open-chain paraffins, which likewise are contained in this stream, are inert and serve the dilution of the reaction mixture, whereby the amount of the added steam can be reduced. This possible reduction of the steam addition has the additional advantage to prolong the useful life of the catalyst, since its irreversible deactivation by dealuminization at the lower steam partial pressure thus obtained is slowed down.

The proportions of the streams discharged from the process usually are less than 10 vol-%, based on the respective total stream, i.e. e.g. 82/80<10 vol-%, 73/75<10 vol-%, 68/66<10 vol-%.

The process shown in FIG. 2 has the advantage that the core system of a usual MTP process as shown in FIG. 1 remains the same and substantially need not newly be designed in terms of engineering. As a result, the quantity of the original MTP gasoline is distinctly reduced and there is obtained a smaller amount of naphtha instead of the usually contained MTP gasoline. The propylene yield of the entire process can distinctly be increased thereby.

Example

Table 1 summarizes the mass balances over the respective plant limits for the prior art process (FIG. 1) and for the improvement according to the invention (FIG. 2):

TABLE 1

| | Process acc. to FIG. 1 [t/h] | | Process acc. to FIG. 2 [t/h] |
|---|---|---|---|
| Feed | | | |
| Methanol | 208.3 | Methanol | 208.3 |
| Products | | | |
| Propylene | 59.3 | Propylene | 71.3 |
| MTP gasoline | 21.5 | MTP naphtha | 7.4 |
| Others* | 10.4 | Others* | 12.5 |
| Water | 117.1 | Water | 117.1 |

*LPG (=$C_3$/$C_4$ paraffins and olefins) and so-called light ends (i.e. methane, $CO_x$, ethane and ethylene)

It can clearly be seen that the improvement of the process according to the invention leads to a distinct increase of the propylene yield.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

LIST OF REFERENCE NUMERALS 1, 2 conduit
3 reactor
4-6 conduit
7 reactor
8 conduit
9 cooler
10 conduit
11 compressor
12, 13 conduit
14 distillation column
15 conduit
20 conduit
21 distillation column
22, 23 conduit
24 distillation column
25, 26 conduit
30 conduit
31 separator
32 conduit
33 column
34-36 conduit
40-42 conduit
46 distillation column
44, 45 conduit
46 distillation column
47-53 conduit
60 distillation column
61, 62 conduit
63 hydrogenation reactor
64 conduit
65 cooling stage
66, 67 conduit
70-75 conduit
80-83 conduit

The invention claimed is:

1. A process for producing olefins from oxygenates, the process comprising the following steps:
   (i) converting, by heterogeneous catalysis, at least one oxygenate to a stream containing propylene, aromatics, and cyclic olefins;
   (ii) separating the stream containing propylene, aromatics, and cyclic olefins into a $C_{5-}$ fraction containing propylene, a $C_{5+}$ fraction containing aromatics and cyclic olefins, and an aqueous fraction containing oxygenates, wherein at least parts of the $C_{5+}$ fraction are supplied to a hydrogenation in step (iii);
   (iii) at least partially hydrogenating the at least parts of the $C_{5+}$ fraction containing aromatics and cyclic olefins to obtain naphthenes; and
   (iv) at least partially recirculating the naphthenes into the heterogeneously catalyzed conversion in step (i).

2. The process according to claim 1, wherein hydrogen is used as hydrogenating agent in step (iii).

3. The process according to claim 2, wherein the hydrogenation is carried out such that parts of a product stream of the hydrogenation are recirculated into the hydrogenation, and that a ratio between the recirculated product stream of the hydrogenation and the at least parts of the $C_{5+}$ fraction containing aromatics and cyclic olefins lies between 1:10 and 10:1 and/or a molar excess of hydrogen lies between 200 and 5000% of the quantity theoretically necessary for the complete saturation of all contained double and aromatic bonds.

4. The process according to claim 2, wherein after step (iv) hydrogen is separated from a product stream of the hydrogenation.

5. The process according to claim 1, wherein from the aqueous fraction containing oxygenates, the oxygenates and water are separated.

6. The process according to claim 5, wherein the separated oxygenates and/or the separated water are/is at least partly recirculated into step (i).

7. The process according to claim 6, wherein the heterogeneously catalyzed conversion is effected in two stages, wherein in the first stage methanol is converted into dimethyl ether and in the second stage dimethyl ether is converted to a stream containing propylene, aromatics and cyclic olefins, and wherein methanol is recirculated to before the first stage and/or water is recirculated in the form of steam to before the second stage.

8. The process according to claim 1, wherein step (ii) further comprising separating the $C_{5+}$ fraction into a $C_{7-}$ fraction and a $C_{7+}$ fraction, and at least parts of the $C_{7+}$ fraction are supplied to step iii and at least parts of the $C_{7-}$ fraction are recirculated to step (i).

9. A process for producing olefins from oxygenates, the process comprising the following steps:
(i) converting, by heterogeneous catalysis, at least one oxygenate to a stream containing propylene, aromatics, and cyclic olefins;
(ii) separating the stream containing propylene, aromatics, and cyclic olefins into a $C_{7-}$ fraction containing propylene and a $C_{7+}$ fraction containing aromatics and cyclic olefins, wherein at least parts of the $C_{7+}$ fraction are supplied to a hydrogenation in step (iii);
(iii) at least partially hydrogenating the at least parts of the $C_{7+}$ fraction containing aromatics and cyclic olefins to obtain naphthenes; and
(iv) at least partially recirculating the naphthenes into the heterogeneously catalyzed conversion in step (i).

10. The process according to claim 9, wherein at least parts of the $C_{7-}$ fraction are recirculated into step (i).

11. The process according to claim 9, wherein the heterogeneously catalyzed conversion is effected in two stages, wherein in the first stage methanol is converted into dimethyl ether and in the second stage dimethyl ether is converted to a stream containing propylene, aromatics and cyclic olefins, and wherein at least parts of the $C_{7-}$ fraction are recirculated after the first stage and before the second stage.

* * * * *